US009504643B2

(12) United States Patent
Tice et al.

(10) Patent No.: US 9,504,643 B2
(45) Date of Patent: Nov. 29, 2016

(54) COMPOSITIONS AND METHODS FOR IMPROVED RETENTION OF A PHARMACEUTICAL COMPOSITION AT A LOCAL ADMINISTRATION SITE

(75) Inventors: Thomas R. Tice, Indiana Springs, AL (US); Kevin W. Burton, Hoover, AL (US)

(73) Assignee: Evonik Corporation, Parsippany, NJ (US)

( * ) Notice: Subject to any disclaimer, the term of this patent is extended or adjusted under 35 U.S.C. 154(b) by 0 days.

(21) Appl. No.: 13/074,542

(22) Filed: Mar. 29, 2011

(65) Prior Publication Data

US 2011/0236497 A1 Sep. 29, 2011

Related U.S. Application Data

(60) Provisional application No. 61/318,574, filed on Mar. 29, 2010.

(51) Int. Cl.
*A61K 9/16* (2006.01)
*A61K 47/36* (2006.01)
*A61K 9/00* (2006.01)

(52) U.S. Cl.
CPC .......... *A61K 9/0024* (2013.01); *A61K 9/1647* (2013.01); *A61K 47/36* (2013.01); *A61K 9/0085* (2013.01); *A61K 9/1652* (2013.01); Y10S 260/31 (2013.01)

(58) Field of Classification Search
None
See application file for complete search history.

(56) References Cited

U.S. PATENT DOCUMENTS

| | | | | |
|---|---|---|---|---|
| 4,014,935 | A * | 3/1977 | Ibbotson | C07D 229/00 502/162 |
| 6,150,581 | A * | 11/2000 | Jiang et al. | 602/50 |
| 6,352,667 | B1 | 3/2002 | English | |
| 6,482,439 | B2 | 11/2002 | Prokop | |
| 6,703,444 | B2 | 3/2004 | Zhao et al. | |
| 7,014,860 | B1 | 3/2006 | Kawata et al. | |
| 7,601,704 | B2 | 10/2009 | Hu et al. | |
| 2002/0013273 | A1* | 1/2002 | Shirley et al. | 514/12 |
| 2003/0059474 | A1* | 3/2003 | Scott et al. | 424/491 |
| 2004/0072793 | A1 | 4/2004 | Aeschlimann et al. | |
| 2004/0265951 | A1* | 12/2004 | Messersmith et al. | 435/68.1 |
| 2005/0152949 | A1* | 7/2005 | Hotchkiss | A61K 9/0024 424/423 |
| 2006/0188583 | A1* | 8/2006 | Lim | A61K 9/0024 424/490 |
| 2006/0233850 | A1 | 10/2006 | Michal | |
| 2006/0240128 | A1* | 10/2006 | Schlagheck | 424/725.1 |
| 2008/0044476 | A1 | 2/2008 | Lyons et al. | |
| 2010/0016257 | A1 | 1/2010 | Brown et al. | |

FOREIGN PATENT DOCUMENTS

| | | | |
|---|---|---|---|
| CN | 101189035 A | 5/2008 | |
| EP | 0539751 A1 | 5/1993 | |
| EP | 1496037 A1 | 1/2005 | |
| IT | WO 2006136905 A2 * | 12/2006 | ............. A61L 27/26 |
| JP | H05124968 A | 5/1993 | |
| JP | 2003531682 A | 10/2003 | |
| JP | 2004-528278 A | 9/2004 | |
| JP | 2008-517927 A | 5/2008 | |
| WO | WO 2006036681 A2 * | 4/2006 | |
| WO | WO2006044342 A2 | 4/2006 | |
| WO | WO 2006136905 A2 * | 12/2006 | |
| WO | WO-2008/041245 A2 | 4/2008 | |

OTHER PUBLICATIONS

I Kolodziejska, B Piotrowska, M Bulge, R Tylingo. "Effect of transglutaminase and 1-ethyl-3-(3-dimethylaminopropyl) carbodiimide on the solubility of fish gelatin—chitosan films." Carbohydrate Polymers, vol. 65, 2006, pp. 404-409.*
SM Berge, LD Bighley, DC Monkhouse. "Pharmaceutical Salts." Journal of Pharmaceutical Sciences, vol. 66 No. 1, Jan. 1977, pp. 1-19.*
Z Mohamadnia, MJ Zohuriaan-Mehr, K Kabiri, A Jamshidi, H Mobedi. "Ionically cross-linked carrageenan-alginate hydrogel beads." Journal of Biomaterials Science Polymer Edition, vol. 19 No. 1, 2008, pp. 47-59.*
Z Zhang, G Huang. "Micro- and Nano-CarrierMediated Intra-Articular Drug Delivery Systems for the Treatment of Osteoarthritis." Journal of Nanotechnology, vol. 2012, Article ID 748909, pp. 1-11.*
International Search Report and Written Opinion issued Mar. 13, 2012 for Intl. App. No. PCT/US2011/030332, filed on Mar. 29, 2011 (Inventor—T. Tice et al.; Applicant—Surmodics Pharmaceuticals, Inc.; pp. 1-13).
Y. Yeo et al: "In Situ Cross-linkable Hyaluronan Hydrogels Containing Polymeric Nanoparticles for Preventing Postsurgical Adhesions", Annals of Surgery, vol. 245, No. 5, May 1, 2007, pp. 819-824.
S.R. Van Tomme et al: "In situ gelling hydrogels for pharmaceutical and biomedical applications", International Journal of Pharmaceutics, Elsevier BV, NL, vol. 355, No. 1-2, May 1, 2008, pp. 1-18, XP026652681, ISSN: 0939-6411, 001: 10.1016/J.EJPD. 2009.06.009 [retrieved on Feb. 7, 2008].
N. Butoescu et al: ""Intra-articular drug delivery systems for the treatment of rheumatic diseases: A review of the factors influencing their performance"", European Journal of Pharmaceutics and Biopharmaceutics, Elsevier Science Publishers B.V., Amsterdam, NL, vol. 73, No. 2, Oct. 1, 2009, pp. 205-218, XP026652681, ISSN: 0939-6411, 001: 10.1016/J.EJPB.2009.06.009 [retrieved on Jun. 21, 2009].

(Continued)

*Primary Examiner* — Isaac Shomer
(74) *Attorney, Agent, or Firm* — Linda S. Li; Jason S. Ngui; Bernard Lau

(57) ABSTRACT

Disclosed herein are compositions comprising cross-linkers for cross-linking a retention vehicle polymer. The compositions are particularly useful for local administration of a bioactive agent, wherein prolonged or extended availability of the bioactive agent at the site of administration is desired. Also disclosed are methods of delivering the compositions to a subject.

21 Claims, No Drawings

(56) References Cited

OTHER PUBLICATIONS

D.A. Rothenfluh et al: "Biofunctional polymer nanoparticles for intraarticular targeting and retention in cartilage", Nat. Mater, vol. 7, No. 3, Mar. 1, 2008, pp. 248-254.

J.H. Ratcliffe et al: "Preparation and evaluation of biodegradable polymeric systems for the intra-articular delivery of drugs", Journal of Pharmacy and Pharmacology, vol. 36, No. 7, Jul. 1, 1984, pp. 431-436.

Cohen, M. et al., "Organization and adhesive properties of the hyaluronan pericellular coat of chondrocytes and epithelial cells," Biophys J, 2003, 85(3): 1996-2005.

McCarron, P.A. et al., "Enhanced surface attachment of protein-type targeting ligands to poly(lactide-co-glycolide) nanoparticles using variable expression of polymeric acid functionality," J. Biomed. Mater. Res. A 2008, 87A: 873-884.

International Preliminary Report Patentabilty issued Oct. 11, 2012 for Intl. App. No. PCT/US2011/030332, filed on Mar. 29, 2011 (Inventor—T. Tice et al.; Applicant—Evonik Degussa Corp.; pp. 1-9).

Greg T. Hermanson, "Bioconjugate Techniques", J. Med.Chem. 1997, vol. 40, p. 631.

"Highly Selective and Orally Active Inhibitors of Type IV Collagenase (MMP-9 and MMP-2): N-Sulfonylamino Acid Derivatives", Tamura et al., J.Med. Chem 1998, vol. 41, p. 640-649.

* cited by examiner

COMPOSITIONS AND METHODS FOR IMPROVED RETENTION OF A PHARMACEUTICAL COMPOSITION AT A LOCAL ADMINISTRATION SITE

CROSS-REFERENCE TO RELATED APPLICATIONS

This application claims the benefit of priority from prior U.S. Provisional Application No. 61/318,574, filed Mar. 29, 2010, the entire contents of which are incorporated herein by reference.

BACKGROUND

Drug delivery vehicles and pharmaceutical compositions are often used to locally deliver bioactive agents to particular locations within a subject. Many vehicles and compositions, however, are difficult to retain locally for extended periods of time. Some formulations can quickly clear (diffuse out of, migrate out of, and/or be removed by one or more active-transport or passive-transport mechanisms) from the site of administration. Rapid clearance of these vehicles and compositions can necessitate their frequent re-administration (re-dosing) in order to provide an effective treatment over a desired duration of days or months. Delivery vehicle and/or drug diffusion away from the site of administration can also induce unwanted side effects, such as inflammatory responses and systemic side effects.

SUMMARY

Disclosed herein are compositions comprising cross-linkers for cross-linking a retention vehicle polymer in a subject, to improve local retention of an active microparticle (i.e., a microparticle containing a bioactive agent) at and/or near the site of administration. The disclosed compositions and methods are particularly useful for local administration of a bioactive agent, wherein prolonged or extended availability of the bioactive agent at the site of administration is desired.

The disclosed compositions comprise: a retention vehicle polymer; and a controlled release cross-linking agent for cross-linking the retention vehicle polymer in situ in a subject, and optionally comprise a biodegradable polymeric microparticle comprising a bioactive agent encapsulated therein.

The disclosed methods comprise administering one or more of the disclosed compositions to a subject.

Also disclosed are microparticles comprising ligands for adhering to a particular tissue, such as a joint tissue, e.g., a knee tissue.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed descriptions are exemplary and explanatory only and are not restrictive.

DETAILED DESCRIPTION

Before the present compounds, compositions, composites, articles, devices and/or methods are disclosed and described, it is to be understood that the aspects described below are not limited to specific compounds, compositions, composites, articles, devices, methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different polymers and agents are disclosed and discussed, each and every combination and permutation of the polymer and agent are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A "bioactive agent" refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. A "releasable bioactive agent" is one that can be released from a disclosed composition. Bioactive agents also include those substances which affect the structure or function of a subject, or a pro-drug, which becomes bioactive or more bioactive after it has been placed in a predetermined physiological environment.

A "cross-linker" refers to an agent that forms a physical or chemical bond between polymer chains of the retention vehicle polymer, either between different polymer chains or between different parts of the same polymer chain. For cross-links made with physical bonds, the cross-linker can dissociate and leave the polymer chain. A "controlled-release cross-linker" is a cross-linker that can replenish dissociated cross-linker and maintain cross-linking with the polymer chain(s) over an extended period of time, e.g., releasing cross-linker for a week, a month or longer, to maintain the structure of retention vehicle polymer.

A "retention vehicle polymer" refers to a polymer that can be cross-linked to form a polymer network that retains a releasable bioactive agent, e.g., a microencapsulated bioactive agent."

In one embodiment, the composition of the invention includes a cross-linking agent for cross-linking a retention vehicle polymer, which can enable prolonged or extended retention of a bioactive agent, e.g., a microencapsulated bioactive agent, at a particular site within a subject. In another embodiment, the composition of the invention includes a microparticle comprising a ligand that can bind or adhere to a tissue of a subject and provide an extended release of a bioactive agent to a local site of administration.

The controlled release cross-linking agent is capable of cross-linking the retention vehicle polymer in situ within a subject for a period of time ranging from 1 day to 3 months or more, for example 2 weeks, 3 weeks, 1 month, 1.5 months, 2 months, 3 months, or more. The extended and controlled release cross-linking activity is attributed to a number of factors, depending on the exact composition. For example, when poorly soluble salts are used as the controlled release cross-linker, as specified herein, the salts slowly dissolve at or near the site of injection and continuously cross-link the retention vehicle polymer over time. Additionally, extended cross-linking can cross-link endogenous polymers, such as hyaluronic acid, which are typically present at or near joints, such as the knee.

In some embodiments, the compositions of the invention include a cross-linker that enables a retention vehicle or a fluid within a subject to effectively retain a pharmaceutical formulation including a bioactive agent, e.g., a microencapsulated bioactive agent, at a desired location for an extended period of time, such as days or even months. The ability to retain the pharmaceutical formulation at a local site for an extended period of time allows for extended therapy, and may reduce the need for re-dosing, as is commonly required in certain locally administered therapies. Local retention of the pharmaceutical composition may also reduce unwanted side effects that can occur when components of the pharmaceutical formulation migrate or otherwise escape the targeted therapeutic site.

The compositions of the invention are particularly useful for areas within a subject, such as a human, that are in or near joints or in or near the subarachnoid area of the brain. When locally administering pharmaceutical compositions to these areas, bioactive agents and other components of pharmaceutical formulations are particularly susceptible to migration or escape from the local site. Examples of locations where the compositions of the invention can provide improved retention include, but are not limited to, the hip, knees, shoulders, ankles, elbows, wrists, toes, fingers, and spinal facet joints, and areas in the brain such as the subarachnoid area.

Joints, in particular, have opposing bones having respective opposing hyaline cartilage articular surfaces, a peripheral, collagenous ligamentous capsule connecting the articular surfaces and defining a central joint space and a synovium lining upon an inner wall of the capsule, and also include synovial fluid contained within the joint space. Synovial fluid contained within the joint space naturally contains polymers, such as hyaluronic acid, that helps to retain pharmaceutical compositions within the joint. However, synovial fluid is frequently regenerated. As synovial fluid regenerates, any pharmaceutical composition including a bioactive agent is susceptible to migration away from or completely out of the joint. Thus, synovial fluid, in of itself, is not optimal for retaining a pharmaceutical composition. The compositions of the invention can be useful in reducing synovial fluid movement and therefore can improve the ability of synovial fluid to retain a pharmaceutical composition or a bioactive agent.

The compositions disclosed herein can result in the local retainment of a biodegradable microparticle containing a bioactive agent (which can be released from the microparticle over time) for a period of time ranging from 1 week to 3 months or longer, i.e., the retention vehicle polymer, by virtue of the cross-linker, can retain the active microparticle at or near the site of original administration for a period of time ranging from 1 week to 3 months or longer. Depending on the nature of the cross-linker and exact composition administered to the subject, active microparticle retention times of 1 week, 2 weeks, 3 weeks, 1 month, 1.5 months, 2 months, 2.5 months, 3 months, or longer, can be achieved. Endogenous retention vehicle polymers produced naturally at or near the site of administration, such as hyaluronic acid naturally produced in or near joints, such as the knee, can be cross-linked to assist in the retention of the active microparticle at the site of injection.

One embodiment of the invention includes a composition suitable for administration to a subject that comprises a controlled release cross-linking agent capable of cross-linking a polymer or higher order polymeric structure, such as a microparticle, to thereby improve retention of a bioactive agent or pharmaceutical composition within a local target area of a subject. In one embodiment, the polymer is already present in a subject and can be a naturally occurring polymer present in the subject. An example is hyaluronic acid, which is a constituent of synovial fluid. The compositions of the invention provide a controlled release cross-linking agent that can cross-link the hyaluronic acid present in synovial fluid and therefore reduce movement of the synovial fluid or the hyaluronic acid. The bioactive agent or pharmaceutical composition can therefore be retained in the synovial fluid for longer periods of time.

The controlled release cross-linking agent can vary in composition depending on the particular retention vehicle for which cross-linking is desired. Generally, the controlled release cross-linking agent has at least two reactive groups or is multivalent, such that the controlled release cross-linking agent is capable cross-linking two or more polymer chains together. The cross-linking can be achieved with physical bonds, such as ionic and/or hydrogen bonds, or the cross-linking can be achieved with chemical bonds. Examples of controlled release cross-linking agents for polysaccharides, charged polymers, or polymers with polar functional groups include a variety of inorganic salts that include multivalent cations and/or anions. Examples include salts of calcium, zinc, strontium, magnesium, barium, manganese, or other multivalent ions. Such salts can comprise any suitable anion, such as chloride, among others.

Other salts that can be used include salts of transition metals, such as Cu(II) and Fe(II). It was observed that such salts can cross-link hyaluronic acids (HA) of varying molecular weights when present in aqueous compositions including from 1-2% by weight hyaluronic acid and from 1-2 mM metal salt (concentration relative to total composition including aqueous component); see Table 1.

TABLE 1

| Metal salt | HA Mw KDa | HA Conc. % | Metal Conc. mM | Observations |
|---|---|---|---|---|
| Fe(II) | 520 | 1 | 1.8 | gel formed |
| | 520 | 2 | 1.8 | gel formed |
| | 1380 | 1 | 1.8 | gel Formed |
| | 1380 | 2 | 1.8 | gel formed |
| Cu(II) | 520 | 1 | 1.8 | gel formed |
| | 520 | 2 | 1.8 | gel formed |
| | 1380 | 1 | 1.8 | gel formed |
| | 1380 | 2 | 1.8 | gel formed |

Specific compositions of the invention include those containing a biodegradable polymeric microparticle (e.g., poly(lactide), poly(glycolide), poly(caprolactone), or a combination or copolymer thereof) comprising a bioactive agent, as specified herein, together with one or more of the hyaluronic acid polymers and metal salts listed in Table 1, in any suitable concentration, such as those listed in Table 1. As discussed elsewhere, such compositions can be injected into a subject to improve local retention of the microparticle containing the bioactive agent, such as in or near a joint, such as the knee, or near certain areas of the brain.

Other suitable controlled release cross-linking agents include small molecules, biomolecules, polymers, or biopolymers with charged or polar functional groups, such as peptides, proteins, and the like. The controlled release cross-linking agent can, in some aspects, have biological activity in of itself, and thus can be a bioactive agent. The controlled release cross-linking agent can also be an inorganic charged or multivalent particle, such as an inorganic microparticle or nanoparticle that is pharmaceutically acceptable. The controlled release cross-linking agent, in some aspects, can be a poorly soluble salt, such as calcium chloride, zinc chloride, or magnesium chloride. The controlled release cross-linking agent can be a bioresorbable microparticle or nanoparticle with charge on its surface. Such cross-linking microparticles or nanoparticles can have bioactive agent inside or no bioactive agent inside. In other aspects, polyethylene glycol (PEG) can be used as a controlled release cross-linking agent. For example, two PEG end-groups can be used to cross-link two or more polymer chains together, such as two or more polysaccharide (e.g., hyaluronic acid) polymer chains.

In some embodiments, the compositions of the invention include the retention vehicle and the controlled release cross-linking agent. The composition including the controlled release cross-linking agent can also be separately administered from another composition that includes the retention vehicle. Suitable retention vehicles include a variety of polymers, such as polyelectrolytes, and polysaccharides, such as hyaluronic acid, alginate, chitosan, collagen, fucans, cellulose, including methylcellulose, hydroxypropylcellulose, hydroxypropylmethylcellulose, carboxymethylcellulose, cellulose acetate phthalate, cellulose acetate succinate, hydroxypropylmethylcellulose phthalate; casein, dextrans, and starches such as amylose and amylopectin, among others. Polyethylene glycol (PEG) can also be used as a retention polymer vehicle.

In one embodiment the retention vehicle is hyaluronic acid (also known as hyaluronan, hyaluronate, and HA), which is an anionic, non-sulfated glycosaminoglycan distributed widely throughout connective, epithelial, and neural tissues. The hyaluronic acid present in the composition can be the same or different than hyaluronic acid that is naturally present in synovial fluid. Polysaccharides such as hyaluronic acid are capable of being cross-linked through a variety of mechanisms, which enhances the viscosity of the formulation and also helps to improve retention in a location of subject. Hyaluronic acid polymers can also function as tissue adhesives such that when the polymer is injected into a tissue, muscle diffusion and migration of the polymer through fascial planes in minimized. See e.g. Cohen et al. Biophys J. 2003; 85: 1996-2005. The tissue adhesion and therefore low tissue migration characteristic of a formulation which comprises hyaluronic acid therefore enables the formulation to remain largely at the administration or injection site. The hyaluronic acid formulations of the invention can therefore limit drug or biologic exposure to surrounding or adjacent non-target tissues, thereby reducing side effects.

Suitable hyaluronic acid polymers include, but are not limited to, hyaluronic acid, modified hyaluronic acid, and sodium hyaluronate. A commercially available example of hyaluronic acid is sold under the tradename ORTHOVISC (available from DePuy Ortho Biotech products, L.P., Raritan, N.J.). Other commercially available hyaluronic acid polymer formulations include JUVEDERM (Allergan), which is an injectable filler comprised a cross-linked hyaluronic acid. Other hyaluronic acid formulations include ORTHOVISC (Anika), DUROLANE (Smith & Nephew), HYALGAN (Sanofi), HYLASTAN (Genzyme), SUPARTZ (Seikagaku/Smith & Nephew), SYNVISC (Genzyme), EUFLEXXA, (Ferring). Many of these commercial products comprise hyaluronic acids of various molecular weights with various degrees of cross-linking of the hyaluronic acid.

The retention vehicle can be cross-linked in the composition, prior to administration to the subject. The retention vehicle can also be non-cross-linked in a first composition and can encounter the cross-linker in the subject and/or can be co-administered with a separate composition that comprises the controlled release cross-linking agent.

Various degrees of retention vehicle cross-linking can be used, e.g., light cross-linking (10% or less) to heavy cross-linking (80% or more). Generally, cross-linking density can be controlled by molecular weight of the retention vehicle polymer (e.g., lower molecular weight polymers can be used to get achieve higher cross-linking density), concentration of the cross-linker, concentration of the polymer, type of cross-linker, or by using one or more cross-linkers, or a combination thereof.

In some embodiments, the retention vehicle can include two or more different polymers that are complexed or cross-linked together. For example, hyaluronic acid polymers can be cross-linked with other polymers, such as alginate. To make such a cross-linked polymer, alginate and hyaluronic acid can be admixed to form a homogeneous solution prior to initiating the cross-linking reaction. Calcium ions, for example, can be added to the reaction mixture, e.g., in the form of a calcium chloride solution, resulting in the formation of ionic cross-links between hyaluronic acid and alginate. Hyaluronic acid and alginate can also be cross-linked via both hydroxyl and carboxyl groups, resulting in ether and ester cross-linking bonds. Other anionic polymers, such as carboxymethylcellulose and gellan gum, and others, can be cross-linked with hyaluronic acid in a similar manner.

In some embodiments, the cross-linker is present in a delivery vehicle that enables controlled or extended release of the controlled release cross-linking agent over time. The delivery vehicle can provide an extended dose of the controlled release cross-linking agent for continuously cross-linking the retention vehicle. For example, a delivery vehicle comprising the controlled release cross-linking agent can be administered along with or separate from a bioactive agent to a joint. The delivery vehicle can provide an extended supply of controlled release cross-linking agent to synovial fluid, such that as the synovial fluid regenerates, fresh synovial fluid can be cross-linked and therefore more effectively retain the bioactive agent or pharmaceutical composition. A similar effect can be achieved with an exogenous retention vehicle that is administered to the subject.

An exemplary formulation for injection comprises a 2% or higher solution of hyaluronic acid (e.g., 2% or higher, 3% or higher, 4% or higher, including 5%, 10%, and 20%) and controlled release cross-linking agent (in any concentration) in an aqueous composition or phosphate-buffered saline (PBS). Such an exemplary formulation can be used to suspend and inject microparticles containing a bioactive agent with good resistance to dispersion in water after the injection. This allows for the active microspheres to stay localized at the site of injection for open surgical procedures, for example. Such formulations can be easily administered at a local site through a small gauge, or large bore, needle, depending on the exact viscosity of the formulation. Alternatively, such a formulation can be administered through a syringe itself (without a needle) at an open site, or a site at which surgery is being carried out, e.g., the tissue of a joint such as a knee during a surgical knee operation, such as knee replacement surgery.

In general, a variety of delivery vehicles can be suitable for providing a controlled or extended release of the controlled release cross-linking agent to the local site of administration. These include implant devices, implantable fibers, rods, viscous pharmaceutical formulations, degradable pharmaceutical carriers, microparticles, nanoparticles, ion-exchange polymers, particles of insoluble salts, and the like.

A preferred delivery vehicle is a biodegradable polymeric microparticle. The controlled release cross-linking agent can be present within or on the microparticle. Two or microparticles can themselves be cross-linked together with a substance that provides the controlled release cross-linking agent as the substance degrades or dissociates, or as the microparticles dissociate from each other. In one example, the microparticle can be associated with or comprise a polymer that is cross-linked with the controlled release cross-linking agent, which can in some aspects, be the retention vehicle polymer. For example, the microparticle can comprise a polysaccharide cross-linked with the controlled release cross-linking agent, such as a hyaluronic acid cross-linked with calcium chloride. Once administered, such a polysaccharide can slowly dissociate to release the controlled release cross-linking agent over time. Such a microparticle can be a nanoparticle or a macroparticle. Furthermore, such particles can also be hydrogels.

Depending on the composition or the mode of administration, the microparticle can comprise the controlled release cross-linking agent and/or the bioactive agent and can in some aspects be present together with the retention polymer. In one embodiment, the composition includes the microparticle comprising the controlled release cross-linking agent. Another composition can be separately administered which includes another microparticle, which can be the same or different, comprising the bioactive agent. Either of these compositions can be administered along with the retention polymer, or can be administered directly into a local site, without the retention polymer or separately from the retention vehicle administration. For example, these compositions can be administered into a joint that contains synovial fluid. The microparticles can also be associated with, or cross-linked with, the retention vehicle polymer. For example, the microparticles can be cross-linked with a hyaluronic acid polymer. In some embodiments, microparticles can be prepared from a suitable retention polymer, such as a polysaccharide. These microparticles can be linked together with the controlled release cross-linking agent, if desired. These microparticles can also contain combinations of the retention polymer and any of the biodegradable polymers disclosed below.

The microparticles generally range in size from 10 nm to 2000 microns. In some examples, the microparticles are from 1 to 80 microns in diameter, from 5 to 60 microns in diameter, or from 10 to 50 microns in diameter.

The microparticles preferably comprise a biodegradable polymer and one or more of a bioactive agent and controlled release cross-linking agent. Suitable biodegradable polymers for use with the invention include without limitation poly(lactide), a poly(glycolide), a poly(lactide-co-glycolide), a poly(caprolactone), a poly(orthoester), a poly (phosphazene), a poly(hydroxybutyrate) a copolymer containing a poly(hydroxybutarate), a poly(lactide-co-caprolactone), a polycarbonate, a polyesteramide, a polyanhydride, a poly(dioxanone), a poly(alkylene alkylate), a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly(oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations thereof.

The biodegradable polymer can comprise one or more residues of lactic acid, glycolic acid, lactide, glycolide, caprolactone, hydroxybutyrate, hydroxyvalerates, dioxanones, polyethylene glycol (PEG), polyethylene oxide, or a combination thereof. More preferably, the hydrophobic polysaccharide derivative is blended with one or more polymers that comprise one or more residues of lactide, glycolide, caprolactone, or a combination thereof.

In some aspects, the biodegradable polymer comprises one or more lactide residues. The polymer can comprise any lactide residue, including all racemic and stereospecific forms of lactide, including, but not limited to, L-lactide, D-lactide, and D,L-lactide, or a mixture thereof. Useful polymers comprising lactide include, but are not limited to poly(L-lactide), poly(D-lactide), and poly(DL-lactide); and poly(lactide-co-glycolide), including poly(L-lactide-co-glycolide), poly(D-lactide-co-glycolide), and poly(DL-lactide-co-glycolide); or copolymers, terpolymers, combinations, or blends thereof. Lactide/glycolide polymers can be conveniently made by melt polymerization through ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

When poly(lactide-co-glycolide), poly(lactide), or poly(glycolide) is used, the amount of lactide and glycolide in the polymer can vary. For example, the biodegradable polymer can contain 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In a further aspect, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide), where the ratios are mole ratios.

In a further aspect, the biodegradable polymer can comprise a poly(caprolactone) or a poly(lactide-co-caprolactone). For example, the polymer can be a poly(lactide-caprolactone), which, in various aspects, can be 95:5 poly(lactide-co-caprolactone), 85:15 poly(lactide-co-caprolactone), 75:25 poly(lactide-co-caprolactone), 65:35 poly(lactide-co-caprolactone), or 50:50 poly(lactide-co-caprolactone), where the ratios are mole ratios.

In a separate embodiment of the invention, a composition comprises a microparticle or nanoparticle comprising a ligand that can bind to a particular tissue, bone or cartilage to enhance retention of the microparticle in a particular location of a subject. For example, a ligand can be conjugated to the surface of the microparticles such that the ligand or targeting moiety binds the microparticles to a specific target, epitope or receptor site on tissue, bone or cartilage. For example, a targeting moiety (e.g. antibody or fragment) can be attached to the polymer directly or via a linker or via a biosensitive linker. The targeting moiety can act to deliver or localize the polymer microparticle to a particular area of a subject. Non-limiting examples of targeting agents or moieties can include folate-binding agents, biotin, albumin, peptides, proteins, polysaccharides, RGD peptides, glycosylated targeting ligands, lipoproteins, antibodies, antibody fragments, enzymes, nucleic acids, aptamers, tumor-specific ligands or peptides, receptor-specific ligands or peptides, among others. Surface functionalization can be accomplished by covalently linking a secondary component to the microparticle.

Covalent linking of a ligand can be achieved by a 3+2 cycloaddition reaction between a reactive moiety on the polymeric microparticle and on the secondary component. For example, the polymeric microparticle can contain a diene moiety and the secondary component can contain a dieneophile. Alternatively, the polymeric microparticle can contain a dieneophile and the secondary component can contain a diene. Covalent linking can be achieved by a 2+2 cycloaddition reaction between a reactive moiety on the polymeric microparticle and on the secondary component.

Covalent linking of a ligand can also involve linking a secondary component to the microparticles through an ether, imidate, thioimidate, ester, amide, thioether, thioester, thioamide, carbamate, disulfide, hydrazide, hydrazone, oxime ether, oxime ester, and/or 30 amine linkage. Such linkages can be formed from known covalent coupling chemistries as amine-reactive chemistries, thiol-reactive chemistries, carboxylate-reactive chemistries, hydroxyl-reactive chemistries, aldehyde, and ketone-reactive chemistries, active hydrogen-reactive chemistries, photoreactive chemical reactions, redox-based chemistries, and the like. In one example, if the secondary component or the polymer particle has an amino group and the other has a carboxylate group, they can be covalently linked via a peptide bond. This can typically be accomplished by using an activating agent to mediate the coupling. Various activating agents that can be used for the coupling reaction include, but are not limited to, 1-ethyl-3-(3-dimethylaminopropyl)carbodiimide (EDC), dicyclohexylcarbodiimide (DCC), N,N-diisopropyl-carbodiimide (DIP), benzotriazol-lyl-oxy-tris-(dimethyl amino)phosphonium hexa-fluorophosphate (BOP), hydroxybenzotriazole (HOBt), and N-methylmorpholine (NMM), including a mixture thereof. The coupling reaction can be carried out in N-methylpyrrolidone (NMP) or in DMF.

In another example, the coupling reaction can involve the treatment of a sulfonamide with a protected hydroxylamine in the presence of EDC, HOBt, and NMM in DMF. See Tamura et at., J Med Chem 1998, 41,640-649, which is incorporated by reference herein for its teaching of amine-acid coupling reactions. Other conjugation techniques are disclosed in Greg T. Hermanson, "Bioconjugate Techniques," Academic Press (Elsevier), 1996, which is incorporated by reference herein for its teaching of conjugation techniques. This embodiment of the invention can be combined with any of the above disclosed compositions and methods.

Generally, the compositions of the invention can be administered in a variety of forms, such as in a sterile aqueous solution or other pharmaceutically acceptable carrier, among others. The aqueous solutions can generally comprise a concentration of about 0.1 to 80 (e.g. 1-20) percent by weight of the formulation or composition (e.g., the delivery vehicle, retention vehicle, cross-linker, or combination thereof). In one example, the formulation has a viscosity of at least about 10 cps, at a shear rate of about 0.1/second. The present formulations are particular useful as injectable formulations, which can be injected into a location of a subject through a delivery device, such as a needle. The size of the needle can be related to the size of the location that is being treated and the formulation properties. In the case of human knee joints, for example, the preferable needle size is about 18 gauge or smaller.

The formulations can be sterilized prior to use. For example, the formulation can be sterilized by common sterilization methods, including ionizing radiation, such as gamma radiation or electron beam radiation, or ethylene oxide (EtO) exposure. Generally, the formulations can be prepared by mixing the components manually or by other mechanical mixing methods, subsequently loading the formulation into a delivery device, such as a syringe, sterilized, and subsequently packaged, as an example method for preparing the formulation.

The mode of administration can be any suitable mode, for example subcutaneous injection, parental administration, enternal administration, and the like. The formulations are preferably injected or simply placed into a subject at a local site. Other conventional delivery modalities include catheters, infusion pumps, pen devices and the like, all of which can be used for local delivery of the formulation.

The compositions generally comprise an "effective amount" of the bioactive agent, which refers to an amount of the formulation that will achieve a desired therapeutic result. The effective amount will vary greatly depending on the composition, bioactive agent, and disorder or condition that is being treated. The actual effective amount of dosage amount of the composition administered to a subject can be determined by physical and physiological factors such as body weight, severity of condition, the type of disease being treated, previous or concurrent therapeutic interventions, idiopathy of the patient and can depend on the route of administration. Depending upon the dosage and the route of administration, the number of administrations of a preferred dosage and/or an effective amount may vary according to the response of the subject. One of skill in the art can determine an effective amount of a disclosed pharmaceutical composition.

The therapeutically effective amount of a formulation for injected into an affected area or treatment site is dependent on several factors, including but not limited to location of the site and the size of the desired area of injection. For example, a therapeutic amount of up to 5 mL of the formulation can be injected or infused into the human intra-articular space of the knee. Formulation volume can be easily adjusted by one of ordinary skill in this art for injections or delivery into other areas, including joints, such as the hip, shoulders, ankles, elbows, wrists, toes, fingers, and spinal facet joints. Up to 10 mL can be injected or infused into the human subarachnoid space.

In some non-limiting examples, a dose of a bioactive agent which is present within a composition of the invention can comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The formulation of the invention can also conveniently contain epinephrine, dexamethasone, or other anti-inflammatory drugs which reduce blood flow at the site of formulation infusion.

The compositions can be administered to any desired subject. The subject can be a vertebrate, such as a mammal, a fish, a bird, a reptile, or an amphibian. The subject of the herein disclosed methods can be, for example, a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered.

Examples of bioactive agents that can be incorporated into the compositions of the invention include, but are not limited to, small molecules, peptides, proteins such as hormones, enzymes, antibodies, antibody fragments, antibody conjugates, nucleic acids such as aptamers, iRNA, siRNA, microRNA, DNA, RNA, antisense nucleic acid or the like, antisense nucleic acid analogs or the like, VEGF inhibitors, macrocyclic lactones, dopamine agonists, dopamine antagonists, low-molecular weight compounds, high-molecular-weight compounds, or conjugated bioactive agents. Bioactive agents contemplated for use in the disclosed compositions include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents include, but are not limited to, peptide drugs, protein drugs, therapeutic antibodies, anticalins, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, anti-inflammatory agents, nonsteroidal anti-inflammatory agents, antiparkinsonian agents, antihypertensive agents, β-adrenergic blocking agents, nutritional agents, anti-TNF agents and the benzophenanthridine alkaloids. The agent can further be a substance capable of acting as a stimulant, sedative, hypnotic, analgesic, anticonvulsant, and the like.

Other bioactive agents include but are not limited to analgesics such as acetaminophen, acetylsalicylic acid, and the like; anesthetics such as lidocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenytoin sodium, diazepam, and the like; antidepressants such as isocarboxazid, amoxapine, and the like; antihistamines such as diphenhydramine HCl, chlorpheniramine maleate, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, Enbrel®, Rituxan®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans. Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Tinidazole, Ropinerole, Ivermectin, Moxidectin, Afamelanotide, Cilengitide, or a combination thereof. In one aspect, the bioactive agent can be a combination of Rifampicin (Rifampin in U.S.) and Minocycline.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. A method for delivering a bioactive agent, comprising: injecting into the subject the following components:
   (a) a first biodegradable polymeric microparticle comprising a bioactive agent encapsulated therein;
   (b) a retention vehicle polymer; and
   (c) a controlled release cross-linking agent which comprises a cross-linking agent dissolved or dispersed in a second biodegradable polymeric microparticle,
   wherein the cross-linking agent cross-links the retention vehicle polymer in situ in the subject and wherein said cross-linking is achieved with ionic bonds wherein the controlled release of the cross-linking agent replenishes dissociated cross-linker and maintains the cross-linking of the retention vehicle polymer thereby prolonging the retention of the bioactive agent; and wherein (i) the cross-linking agent comprises a charged peptide or charged protein; or (ii) the cross-linking agent is a bioresorbable microparticle or nanoparticle with a charge on its surface; or (iii) the cross-linking agent is a multivalent ion, wherein the bioactive agent is selected from the group consisting of an anti-inflammatory agent, an analgesic, an anesthetic, an anti-infective agent, an anti-cancer agent, and a cardiovascular agent, and with the proviso that the bioactive agent is not a growth factor, a tissue growth agent, nor insulin.

2. The method of claim 1, wherein the first or second biodegradable polymeric microparticle is selected from the group consisting of poly(lactide), poly(glycolide), poly(lactide-co-glycolide), poly(caprolactone), or a copolymer, mixture, or blend thereof.

3. The method of claim 1, wherein the bioactive agent, retention vehicle polymer, and controlled release cross-linking agent are injected into the joint or subarachnoid area of the brain of a subject.

4. The method of claim 1, wherein the controlled release cross-linking agent comprises a salt comprising a multivalent ion.

5. The method of claim 1, wherein the controlled release cross-linking agent comprises a charged peptide or charged protein.

6. The method of claim 1, wherein the retention vehicle polymer is a hyaluronic acid.

7. The method of claim 4, wherein the multivalent ion is selected from the group consisting of calcium, zinc, strontium, magnesium, barium, manganese, copper, iron, and combinations thereof.

8. The method of claim 1, wherein the controlled release cross-linking agent comprises calcium chloride, zinc chloride, or magnesium chloride.

9. The method of claim 1, wherein the bioactive agent, retention vehicle polymer, and controlled release cross-linking agent are administered in the same composition.

10. The method of claim 1, wherein the retention vehicle polymer and controlled release cross-linking agent are separately administered from the bioactive agent.

11. The method of claim 10, wherein the retention vehicle polymer and controlled release cross-linking agent are administered in the same composition.

12. The method of claim 6, wherein the retention vehicle polymer further comprises alginate.

13. The method of claim 3, wherein the joint is selected from the group consisting of the shoulder and the knee.

14. The method of claim 1 in which the subject is a human.

15. The method of claim 1, wherein the bioactive agent is an anti-inflammatory agent.

16. The method of claim 15, wherein the anti-inflammatory agent is a steroidal anti-inflammatory agent.

17. The method of claim 15, wherein the anti-inflammatory agent is a non-steroidal anti-inflammatory agent.

18. The method of claim 1, wherein the anesthetic is lidocaine, xylocaine, or combinations thereof.

19. The method of claim 1, wherein the analgesic is acetaminophen, acetylsalicylic acid, or combinations thereof.

20. The method of claim 16, wherein the steroidal anti-inflammatory agent is methylprednisone.

21. The method of claim 17, wherein the non-steroidal anti-inflammatory agent is ibuprofen.

* * * * *